(12) United States Patent
Chen

(10) Patent No.: US 8,880,141 B2
(45) Date of Patent: Nov. 4, 2014

(54) PHOTOACOUSTIC IMAGING DEVICES AND METHODS OF MAKING AND USING THE SAME

(75) Inventor: Jingkuang Chen, Rochester, NY (US)

(73) Assignee: STC. UNM, Albuquerque, NM (US)

( * ) Notice: Subject to any disclaimer, the term of this patent is extended or adjusted under 35 U.S.C. 154(b) by 321 days.

(21) Appl. No.: 12/995,313

(22) PCT Filed: Jun. 1, 2009

(86) PCT No.: PCT/US2009/045835
§ 371 (c)(1),
(2), (4) Date: Feb. 28, 2011

(87) PCT Pub. No.: WO2009/158146
PCT Pub. Date: Dec. 30, 2009

(65) Prior Publication Data
US 2011/0190617 A1 Aug. 4, 2011

Related U.S. Application Data

(60) Provisional application No. 61/057,569, filed on May 30, 2008, provisional application No. 61/100,981, filed on Sep. 29, 2008.

(51) Int. Cl.
*G01N 29/00* (2006.01)
*A61B 8/00* (2006.01)
*A61B 5/00* (2006.01)
*G01N 29/24* (2006.01)

(52) U.S. Cl.
CPC ............. *A61B 5/0095* (2013.01); *A61B 5/0048* (2013.01); *A61B 5/0093* (2013.01); *A61B 8/44* (2013.01); *A61B 8/4483* (2013.01); *G01N 29/24* (2013.01); *G01N 29/2406* (2013.01); *G01N 29/2418* (2013.01); *A61B 2562/02* (2013.01); *A61B 2562/028* (2013.01)
USPC ............ 600/407; 600/437; 600/459; 367/181

(58) Field of Classification Search
USPC .......................................... 600/437, 407, 459
See application file for complete search history.

(56) References Cited

U.S. PATENT DOCUMENTS

| 4,267,732 A | 5/1981 | Quate |
| 4,512,197 A | 4/1985 | von Gutfeld et al. |
| 5,718,226 A * | 2/1998 | Riza .............................. 600/437 |

(Continued)

FOREIGN PATENT DOCUMENTS

EP  0 339 885 A2  11/1989

OTHER PUBLICATIONS

Martin A. Green, Self-consistent optical parameters of intrinsic silicon at 300K including temperature coefficients, Solar Energy Materials and Solar Cells, vol. 92, Issue 11, Nov. 2008, pp. 1305-1310.*

*Primary Examiner* — Long V. Le
*Assistant Examiner* — Michael Kellogg
(74) *Attorney, Agent, or Firm* — Schwegman Lundberg & Woessner, P.A.

(57) ABSTRACT

A photoacoustic imaging device includes an array of light sources configured and arranged to illuminate a target region and an array of ultrasonic transducers between the array of light sources and the target region. The array of transducers may be fixedly coupled to the array of light sources, and the array of ultrasonic transducers may be configured and arranged to receive ultrasound transmissions from the target region.

18 Claims, 12 Drawing Sheets

(56) References Cited

U.S. PATENT DOCUMENTS

| | | |
|---|---|---|
| 6,945,114 B2 | 9/2005 | Kenderian et al. |
| 2005/0177045 A1* | 8/2005 | Degertekin et al. ............ 600/457 |
| 2005/0187471 A1* | 8/2005 | Kanayama et al. ............ 600/437 |
| 2007/0287912 A1* | 12/2007 | Khuri-Yakub et al. ........ 600/439 |

* cited by examiner

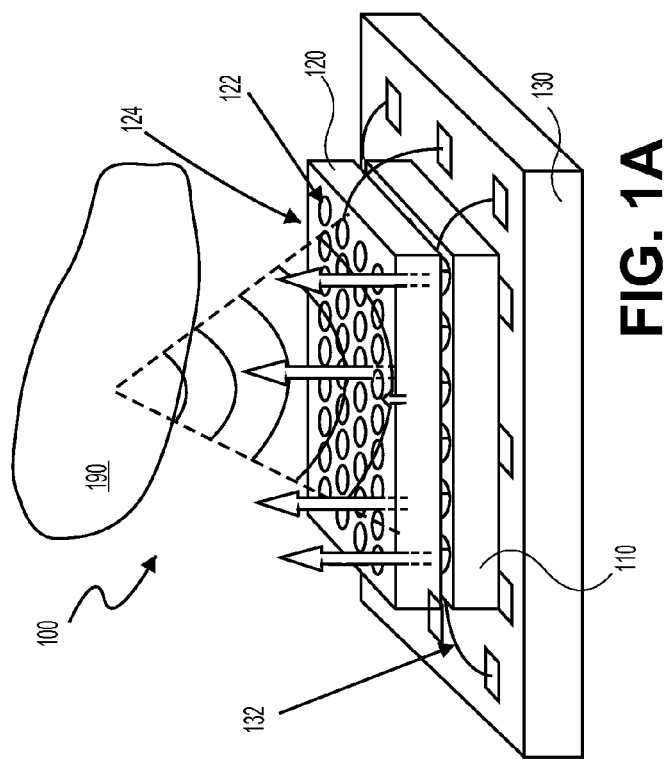
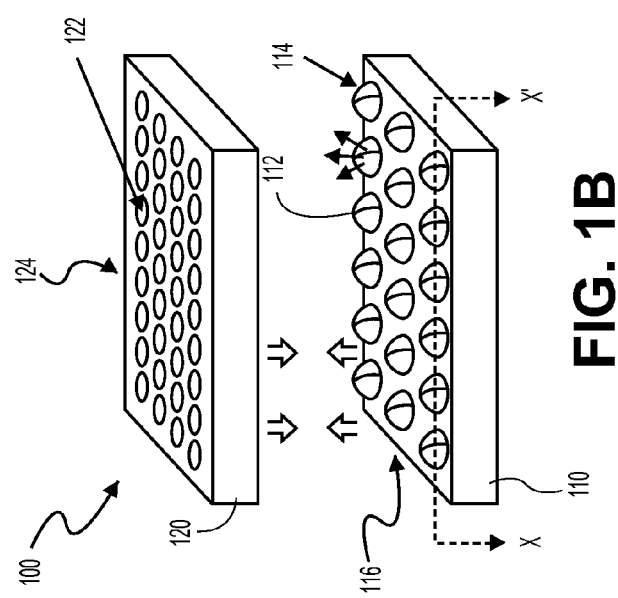
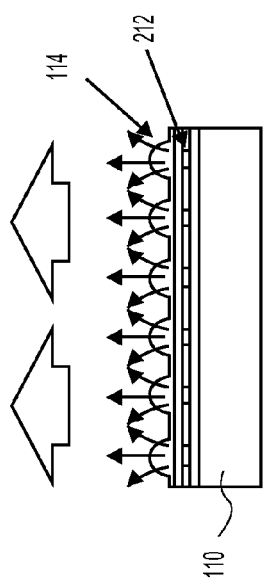
FIG. 1A
FIG. 1B
FIG. 1C

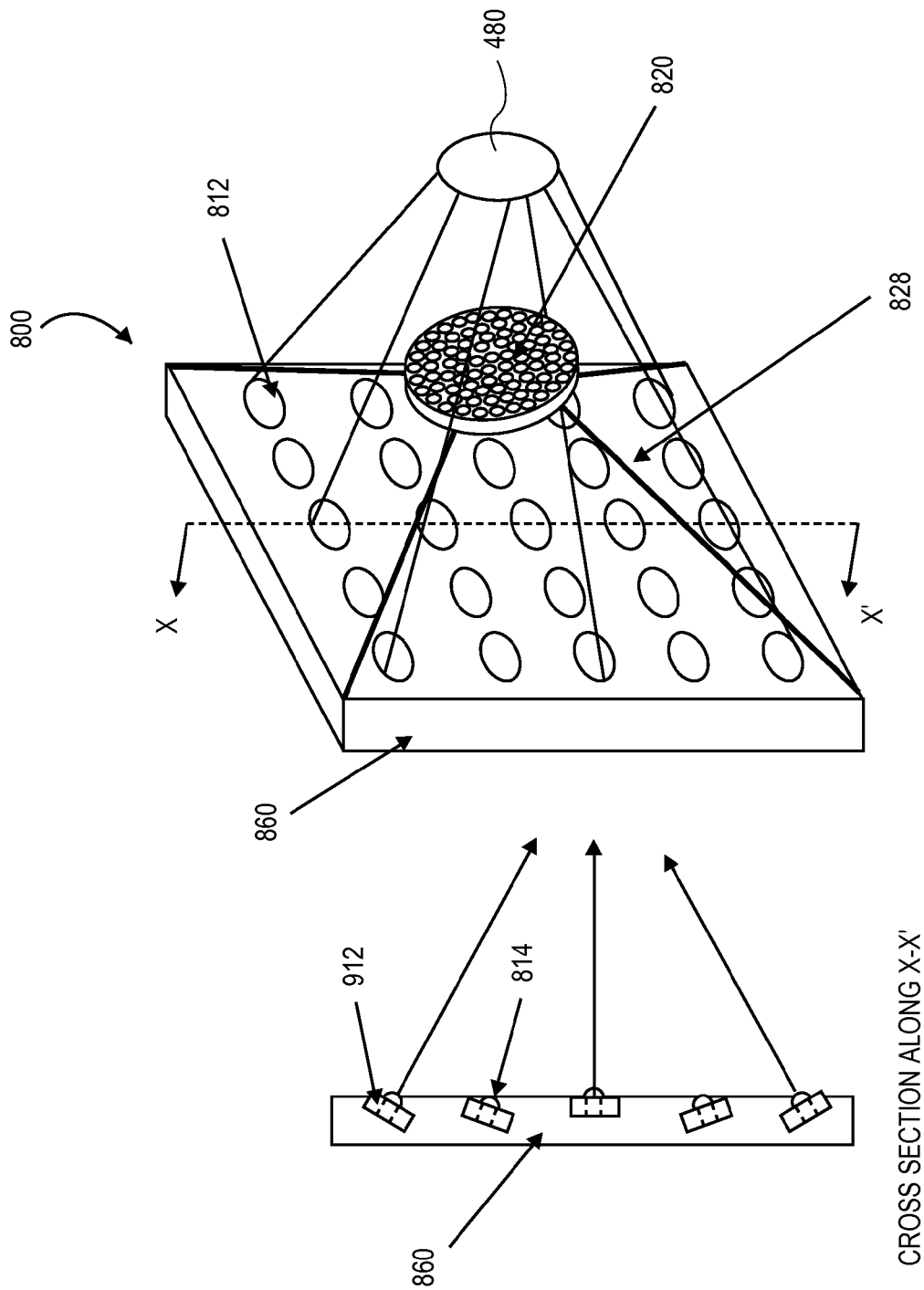

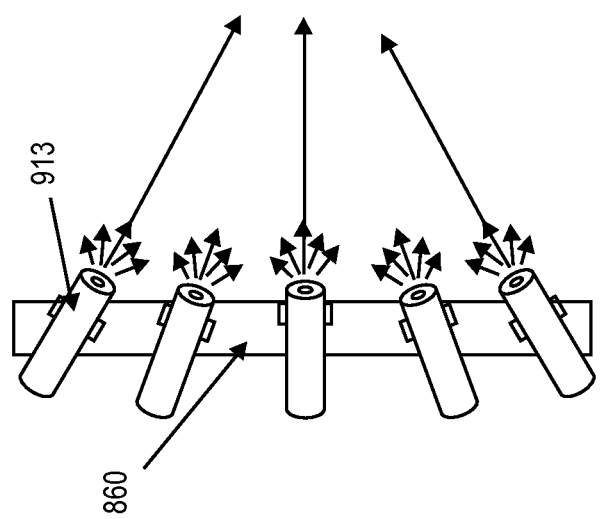

PHOTOACOUSTIC IMAGING DEVICES AND METHODS OF MAKING AND USING THE SAME

CROSS-REFERENCE TO RELATED APPLICATIONS

This application is filed under 35 U.S.C. §371 as a U.S. national phase application of PCT/US2009/045835, having an international filing date of Jun. 1, 2009, which claims the benefit of U.S. provisional patent application number 61/057,569, filed on May 30, 2008, and U.S. provisional patent application number 61/100,981, filed on Sep. 29, 2008, the contents of both of which are incorporated herein by reference.

TECHNICAL FIELD

The present disclosure relates generally to photoacoustic imaging. More particularly, this disclosure relates to photoacoustic imaging devices, including photoacoustic modules having a light source and an ultrasonic transducer array, and methods of imaging with these devices.

BACKGROUND

Photoacoustic imaging (PAI) makes use of infrared-induced ultrasound for constructing an image of an organ or tissue inside the body. In this process, a short infrared pulse, typically 5-10 ns in width, is used to illuminate the organ or tissue. Upon absorption of infrared energy, the tissue heats up and expands. This instantaneous tissue expansion generates ultrasound, which is received by an ultrasound transducer for image formation. Photoacoustic imaging makes use of the difference of infrared absorption rate of different tissues and may provide better image contrast than pulse-echo ultrasound imaging. Due to the high infrared absorption rate of hemoglobin, a photoacoustic imaging process may be useful in imaging blood-containing organs/tissue and may therefore be useful for identifying disease symptoms related to blood, including early-stage tumors or internal bleeding.

As a promising new technology, photoacoustic imaging is gaining ground in clinical use and has been proved to be useful in providing critical diagnostic information (mainly due to its blood "seeing" capability) not available from traditional medical imaging modalities including X-ray and pulse-echo ultrasound. Currently, one common practice of performing photoacoustic imaging uses a laser light source for tissue illumination and a separately positioned ultrasound transducer for receiving the ultrasound transmitted from the infrared-stimulated tissue. The laser light source, the ultrasonic transducer, and the target tissue are manually aligned in order to obtain the maximum ultrasound signal. While useful as a laboratory platform, this setup is not suitable for an end user like a medical doctor for general clinical use.

It may be desirable to provide a photoacoustic imaging device that integrates a broad-area infrared light source with a microelectromechanical systems-based ultrasonic transducer array in a package for medical imaging. Similar to a camera with a built-in flash light, the relative position between the infrared light source and the ultrasonic transducers on the integrated device may be accurately aligned with both devices being aimed at the target direction. Thus, the integrated photoacoustic imaging device can be placed on the skin of the patient for imaging, and no infrared light source to ultrasound transducer alignment is needed.

It may be desirable to provide the integrated imaging device with an integrated front-end signal-processing circuit so that the device can provide portable, real-time, three-dimensional photoacoustic imaging of an organ or tissue for clinical use. It may be desirable to display the three-dimensional images acquired by the imaging device in real time and/or to store the images, for example, in a personal computer, for future review.

It may be desirable to provide the integrated photoacoustic imaging device with pulse-echo ultrasound imaging in parallel with the photoacoustic imaging so as to offer complementary diagnostic information.

PAI is also gaining ground as a potential replacement for mammography. Breast cancer is a cancer that starts in the cells of the breast. Worldwide, amongst both sexes combined, breast cancer is the second most common type of cancer after lung cancer and the fifth most common cause of cancer death. Women in the United States have the highest incidence rates of breast cancer in the world. Among women in the US, breast cancer is the most common cancer and the second-most common cause of cancer death (after lung cancer). In 2007, breast cancer was expected to cause 40,910 deaths in the US (7% of cancer deaths; almost 2% of all deaths).

While mammography is the only breast cancer screening method that has been shown to save lives, it is not perfect and has its limitations. First, estimates of the numbers of cancers missed (false-negative) by mammography are usually around 10%-20%. Mammography cannot detect small tumors with diameters less than 4 mm at their earliest stages. Tumors of early stage are generally soft and embedded in soft tissue, so the cancer is easily hidden by other dense tissue in the breast and even after retrospective review of the mammogram, cannot be seen. Also, because the X-ray contrast between the early tumor tissue and normal tissue types is low, it is hard for the mammography to detect the early stage tumors. In order to be reliably detected by traditional X-ray-based mammography, the tumor must be large and have a high density. The technique is further challenged by the age of the woman; younger women have denser breast tissue, making masses harder to detect. Furthermore, one form of breast cancer, lobular cancer, has a growth pattern that produces shadows on the mammogram which are indistinguishable from normal breast tissue.

Second, mammography often fails to differentiate conclusively between malignant and benign masses (false positive) which will cause women to undergo unnecessary medical intervention and undue stress. It helps to know these approximate statistics: of every 1,000 U.S. women who are screened, about 7% (70) will be called back for a diagnostic session (although some studies estimate the number closer to 10%-15%). About 10 of these will be referred for a biopsy; the remaining 60 are found to be of benign cause. Of the 10 referred for biopsy, about 3.5 will have a cancer and 6.5 will not. Of the 3.5 who do have cancer, about 2 have a low stage cancer that will be essentially cured after treatment.

Breast cancer has a very characteristic pathophysiological profile. A malignancy is highly vascularized. When a tumor is malignant, it develops rapidly and needs a lot of nourishment and oxygen. To supply these components, tumors develop a microcirculation network through a process called angiogenesis. This network helps the tumor withstand an immune system attack and continue its aggressive growth. The presence of this network also means that the tumor will have a concentration of blood that ranges from two to six times the amount expected in normal breast tissue. The second differentiating characteristic of a breast tumor is a function of the tumor's hunger for oxygen. The blood in the tumor is oxygen depleted, or hypoxic. Oxygenated blood has a different infrared absorption coefficient than hypoxic blood. Finally, visualizing the mass accurately gives the best indication of its shape, which is another clue to malignancy. A smooth, symmetrical shape holds the best news, while an irregularly shaped mass indicates trouble. When the shape is very ugly, it is a strong indication of malignancy. When it is round or elliptical, the mass has been encapsulated by the immune system, indicating a benign tumor. While irregular blood vessel distribution and blood oxygen concentration provide the surest indication of breast cancer, conventional X-ray-based mammography or ultrasound imaging cannot distinguish blood from tissue and therefore would miss this valuable diagnostic information. While magnetic resonance imaging (MRI) is capable of capturing the image of blood, the equipment and operation cost of MRI is too expensive for regular annual breast screenings, which are recommended for women above the age of 40.

Photoacoustic imaging provides an affordable solution to this problem. PAI uses a short pulse of light to generate acoustic waves that are used to form an image. In this process, the target object is flashed with a laser pulse on the order of 5 nanoseconds, leading to optical absorption (typically a fraction of a degree Celsius) and thermo-elastic expansion. This expansion generates ultrasound, which can be detected by an ultrasound transducer or an array of receivers to form a three-dimensional (3-D) image. Whereas traditional pulse-echo ultrasound imaging has low contrast in soft tissue due to similar acoustic impedances, PAI benefits from high optical contrast combined with excellent spatial resolution determined primarily by the ultrasound wavelength, approaching cellular resolution. Contrast in PAI depends primarily on the optical wavelength and absorption spectrum of the tissue. Thus, PAI provides an appreciably higher contrast than pulse-echo ultrasonic imaging. Moreover, when the light source is tuned to the near infrared, PAI can be used to form an image well over a centimeter into tissue. One-way propagation of ultrasound is used to carry the information back to the ultrasound receiver(s), and conventional beamforming based on time delays can be used to create an image.

For photoacoustic imaging of live human or animal tissue with red blood cells, hemoglobin provides significant help in boosting the contrast ratio. Hemoglobin has a very high optical contrast in the visible and infrared spectra. As a result, high-contrast imaging of blood containing structures in tissue such as tumors or blood vessel is one of the unique advantages of PAI. Due to making use of this blood concentration/content related optical absorption, PAI is exceptionally useful for identifying diseases/abnormalities related to blood, such as internal bleeding from stroke or early-stage cancer. Doctors can use PAI to recognize many problems that are difficult to identify using conventional diagnostic techniques, such as pulse echo ultrasound, x-ray or magnetic resonance (MR).

Compared to other techniques, PAI is a safe process that uses nonionizing radiation and fluences within standards set by ANSI and could provide 3-D images with high resolution and contrast. In addition to viewing anatomical structure, photoacoustic imaging is capable of detecting composition of tissue and functional activities of an organ based on blood-related infrared absorption rate difference and sensitivity of the optical spectrum of hemoglobin to oxygenation saturation.

Photoacoustic imaging forms an image of an object using ultrasound transmitted from the object in a light induced heating process. Involving interactions between photons, ultrasound, and an object, photoacoustic imaging is non-ionizing and capable of viewing anatomical structures in tissue with improved image contrast than that from pulse-echo ultrasound imaging. Photoacoustic imaging works by flashing a short-pulsed near-infrared laser at low energy onto a target tissue. The long wavelength of near infrared light allows light to penetrate deep into the tissue. As the light is absorbed by tissue, the tissue heats up and expands through a process called rapid thermo-elastic expansion. This instantaneous tissue expansion creates ultrasonic waves which can be received by an ultrasound detector array. The received acoustic signals can be interpreted using beam-forming algorithms to generate 2-D or 3-D images of the target tissue. With contrast based on optical absorption, and sub-mm spatial resolution, photoacoustic imaging offers attractive attributes for imaging biological tissue. When a near-infrared (NIR) laser source is used, it has an added benefit of excellent penetration into biological tissue of several centimeters.

Compared to traditional pulse-echo ultrasound imaging, photoacoustic imaging provides optical contrast with good penetration and high spatial resolution, making it an attractive tool for non-invasive applications in medical diagnosis, especially for unique applications such as high blood concentration identification. By combining with intravascular ultrasound (IVUS) imaging, photoacoustic imaging can visualize both morphological and functional changes of the vulnerable plagues in the vessel, and thus can be used for invasive applications.

Photoacoustic imaging is a promising new technology that will likely find its way soon to the clinical arena for human use. One of the current limitations of PAI for general clinical use is developing the technology and hardware that would provide fast, real-time anatomical or functional images. This is critical to extend PAI to be used on. Currently one of the most common practices for photoacoustic imaging is using a near-infrared laser, such a Q-switched Nd:YAG laser or a laser diode coupled to an optical fiber or a lens, to illumine the target biological object. A separately located ultrasonic transducer (or an array of receivers) is used to detect the ultrasound emitted by the tissue. Manual alignments between the infrared source, the ultrasound transducer, and the target tissue are needed. Manual alignment/adjustment is time consuming and does not always produce satisfactory results. In addition, few existing systems allow for full parallel receive that would provide a 3D image from a single laser pulse.

Medical doctors would benefit most from a simple system and device that provides real-time PAI. A system that integrates both the light illumination and ultrasound receiving array together would facilitate PAI, especially for human use.

The current photoacoustic imaging mainly relies on single piezoelectric transducer for the ultrasound detection. However, the device performance of the piezoelectric ultrasonic transducer in medical applications is limited by the material properties and related electrical and acoustic impedance match issues. The fabrication of piezoelectric transducer array requires meticulous handcrafting. Relatively recently, capacitive micromachined ultrasonic transducers (CMUTs) have emerged as a promising alternative. Extensive research on the fabrication and modeling of CMUTs began in the early 1990s. Except for the inherent advantages such as the broader bandwidth, higher sensitivity over piezoelectric counterpart, CMUT technology provides a promising approach to manufacturing densely populated array and realization of high-frequency imaging probes using standard micro-fabrication techniques such as photolithography and thin film deposition. This high frequency CMUT probe can be the answer to the demand of high-resolution imaging system for invasive applications such as the combination of photoacoustic and intravascular imaging system.

It may be desirable to continue development of a miniature capacitive micromachined ultrasonic transducer (CMUT) array for photoacoustic imaging (PAI). As a minimally invasive imager, such a device may be capable of receiving relatively weak ultrasound signals that are difficult to access with non-invasive transducers and may be useful for acquiring photoacoustic images of biological structures deep inside the tissue or inside an organ.

It may further be desirable to fabricate a CMUT imager probe using a two-layer polysilicon surface micromachining process, followed by a double-sided deep silicon etching process for shaping the silicon substrate into a thin probes. It maybe desirable to develop new CMUT structures for an implantable imager probe, aiming at reducing the effective gap height and the driving voltage, as well as alleviating the charging trap effect.

This disclosure solves one or more of the aforesaid problems with a photoacoustic imaging device that integrates a broad-area infrared light source with a microelectromechanical systems-based ultrasonic transducer array.

SUMMARY OF THE INVENTION

According to various aspects, the present disclosure is directed to a photoacoustic imaging device comprising an array of light sources configured and arranged to illuminate a target region and an array of ultrasonic transducers between the array of light sources and the target region. The array of transducers may be fixedly coupled to the array of light sources, and the array of ultrasonic transducers may be configured and arranged to receive ultrasound transmissions from the target region.

According to some aspects, a method of photoacoustic imaging may include transmitting light through a substrate comprising ultrasonic transducers and toward a target region, receiving ultrasonic transmissions generated by the target region, and generating an image representative of the target region based on the received ultrasonic transmissions.

In various aspects, a photoacoustic imaging system may comprise a planar array of ultrasound elements based on capacitive micromachined ultrasonic transducer (CMUT) technology and an integrated light delivery system in the same package. Such an imaging system could provide real-time 3-D images of the breast and other anatomical structure of the body for clinical use. In addition to anatomical structure and distribution of blood vessels in breast, this imaging system would be capable of detecting hemoglobin oxygenation and therefore may be useful for early-stage breast cancer screening.

BRIEF DESCRIPTION OF THE DRAWINGS

FIG. 1A is a schematic illustration of an exemplary photoacoustic imaging device in accordance with various aspects of the disclosure.

FIG. 1B is an exploded view of a portion of the exemplary photoacoustic imaging device of FIG. 1A.

FIG. 1C is a cross-sectional view along line X-X' of FIG. 1A.

schematic illustration of an exemplary photoacoustic imaging device in accordance with various aspects of the disclosure.

Figure 2A:
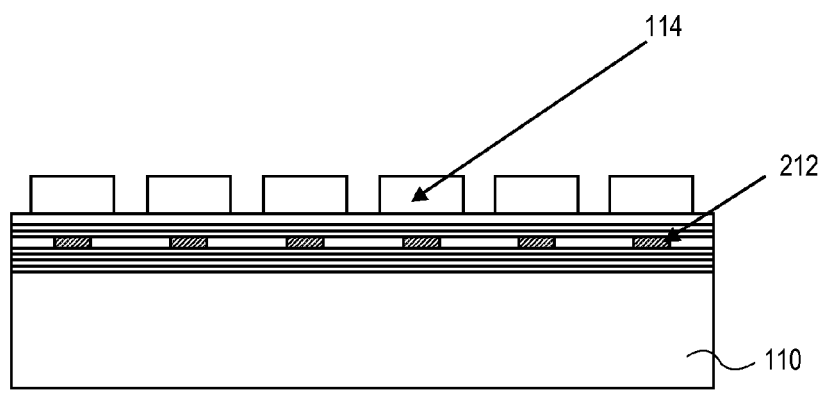
Figure 2B:
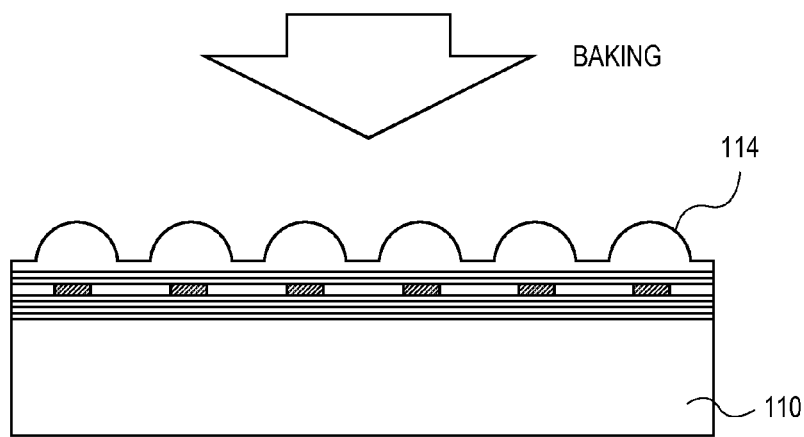

FIGS. 2A and 2B are schematic illustrations of an exemplary process of fabricating an array of micro lenses on the substrate of FIG. 1 that includes an array of laser diodes.

Figure 3A:
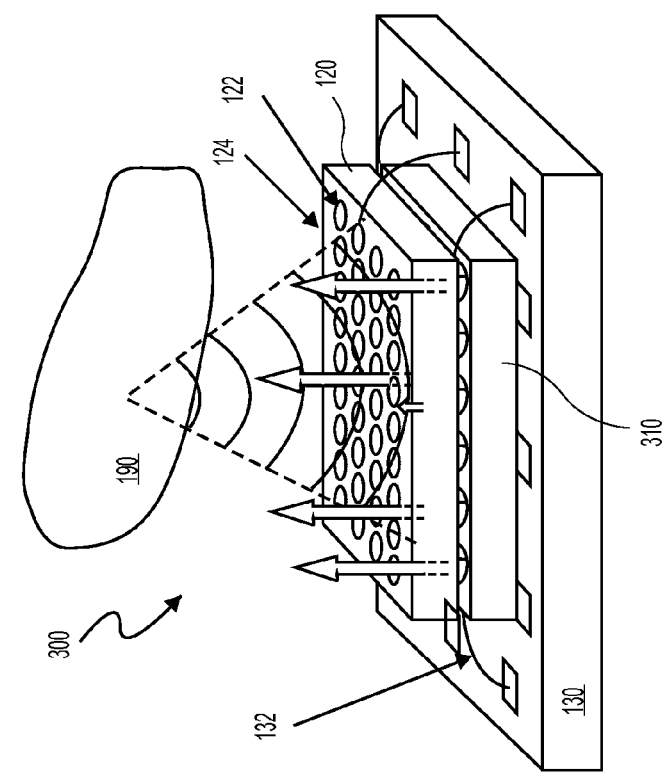

FIG. 3A is a schematic illustration of an exemplary photoacoustic imaging device in accordance with various aspects of the disclosure.

Figure 3B:
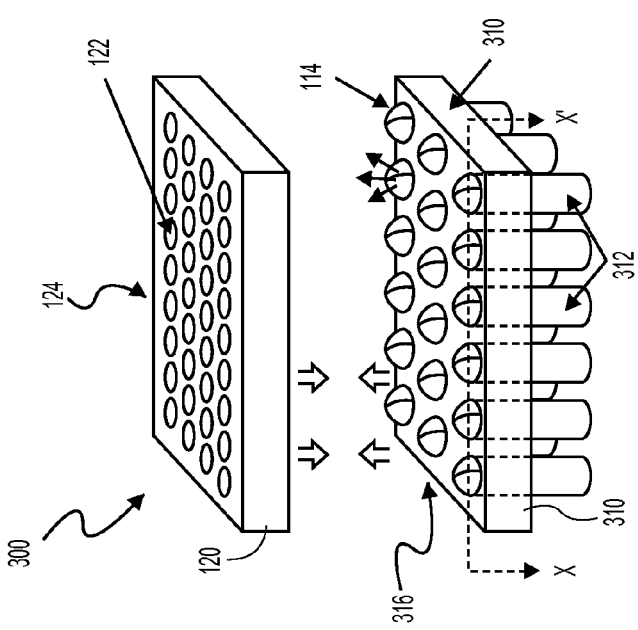

FIG. 3B is an exploded view of a portion of the exemplary photoacoustic imaging device of FIG. 3A.

Figure 3C:
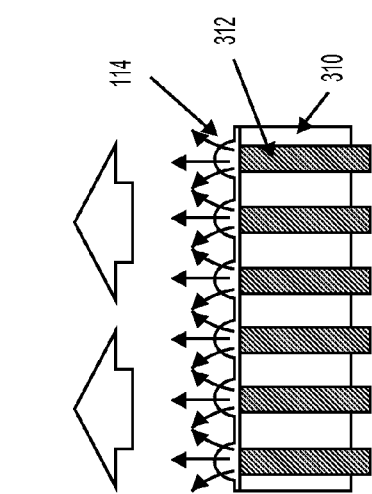

FIG. 3C is a cross-sectional view along line X-X' of FIG. 3A.

Figure 4B:
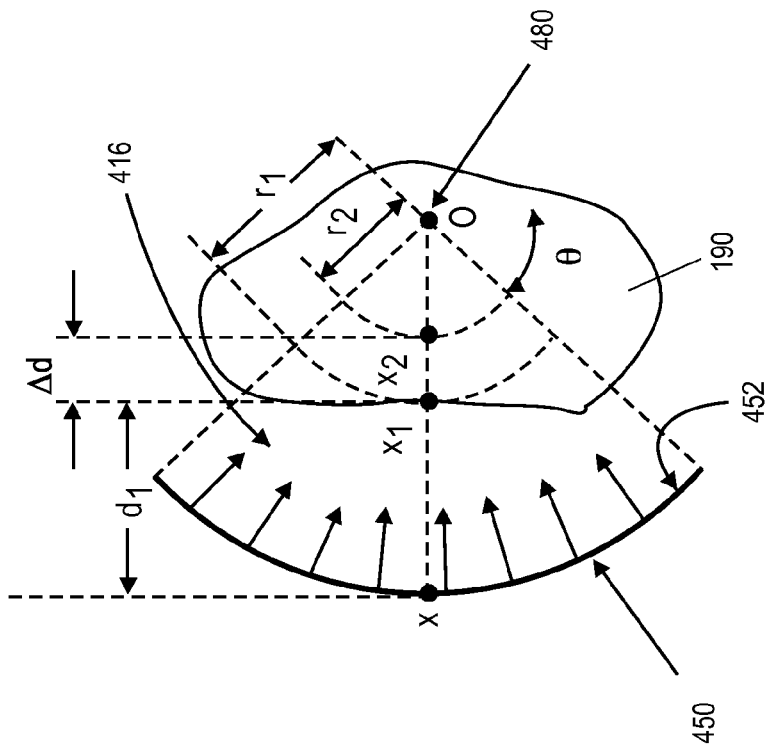
Figure 4A:
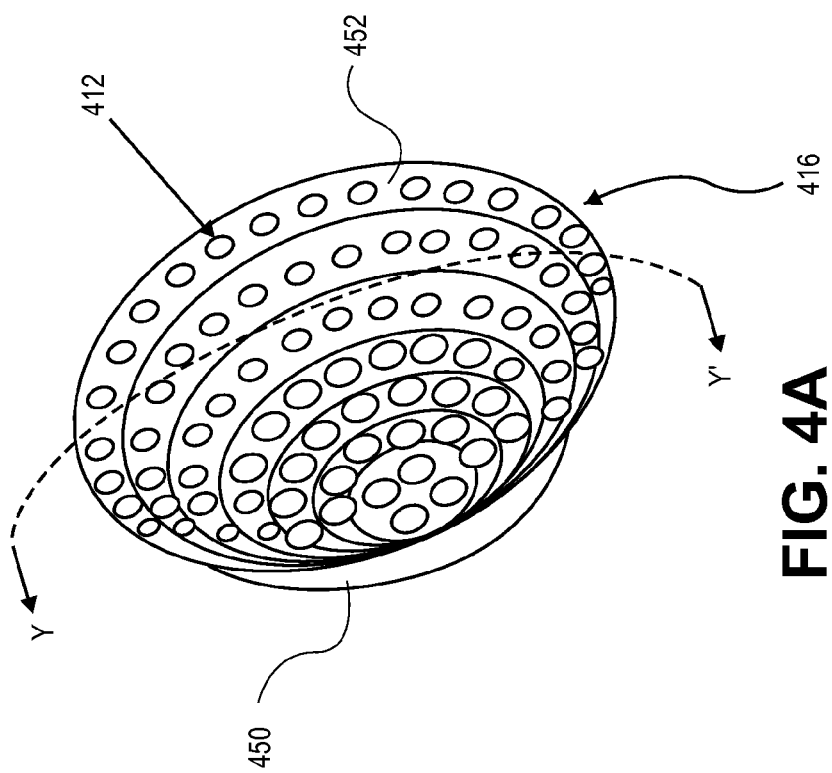

FIG. 4A is a schematic illustration of an exemplary curved alignment of an array of infrared light sources for a photoacoustic imaging device in accordance with various aspects of the disclosure.

FIG. 4B is a cross-sectional view along line Y-Y' of FIG. 4A.

Figure 5:
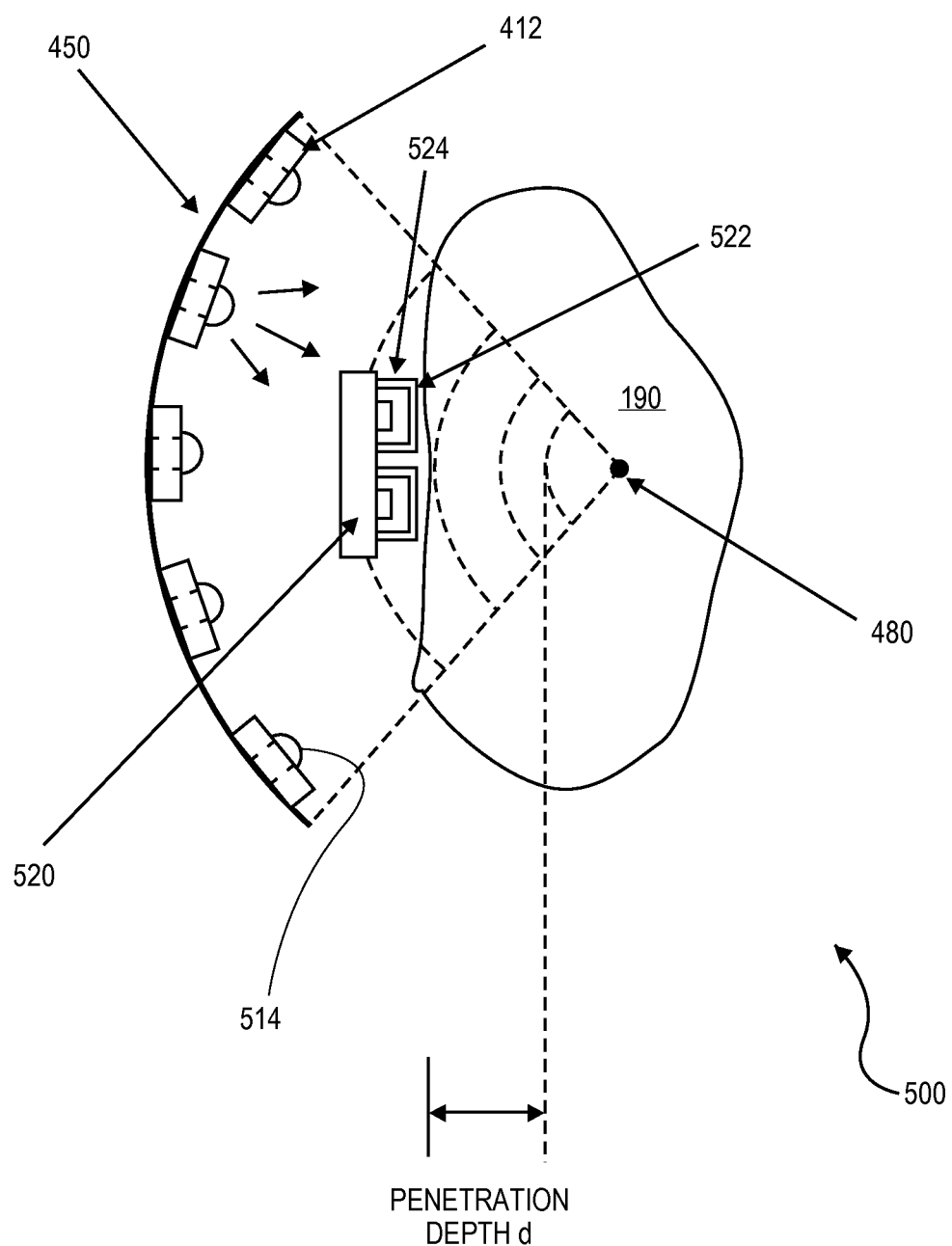

FIG. 5 is a schematic illustration of an exemplary curved alignment of an array of infrared light sources and an array of ultrasonic transducers for a photoacoustic imaging device in accordance with various aspects of the disclosure.

Figure 6A:
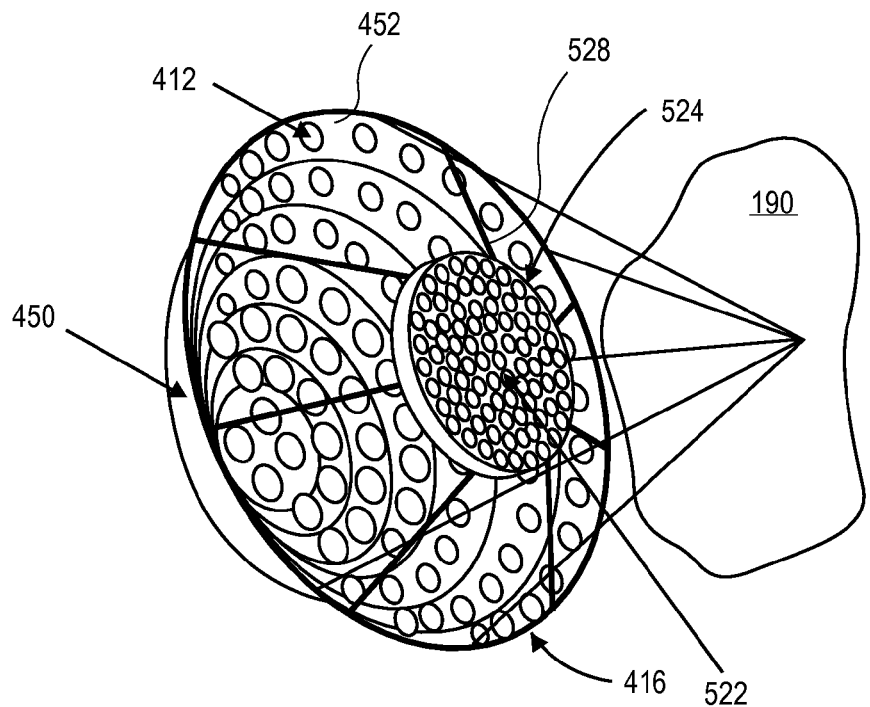
Figure 6B:
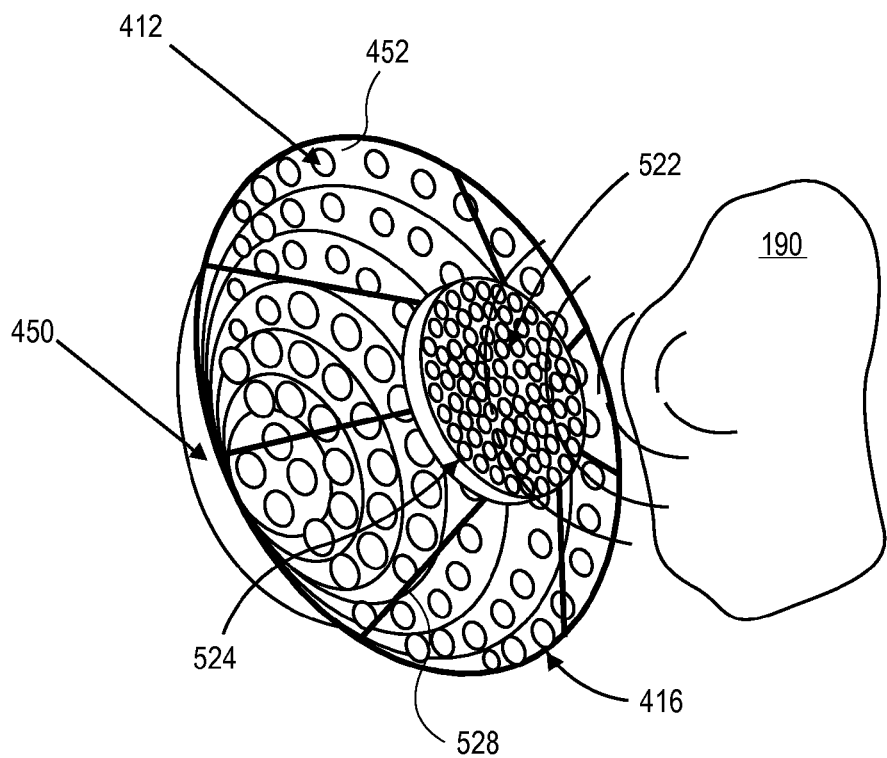

FIGS. 6A and 6B are schematic illustrations of an exemplary photoacoustic imaging device being used to image a tissue in accordance with various aspects of the disclosure.

Figure 7A:
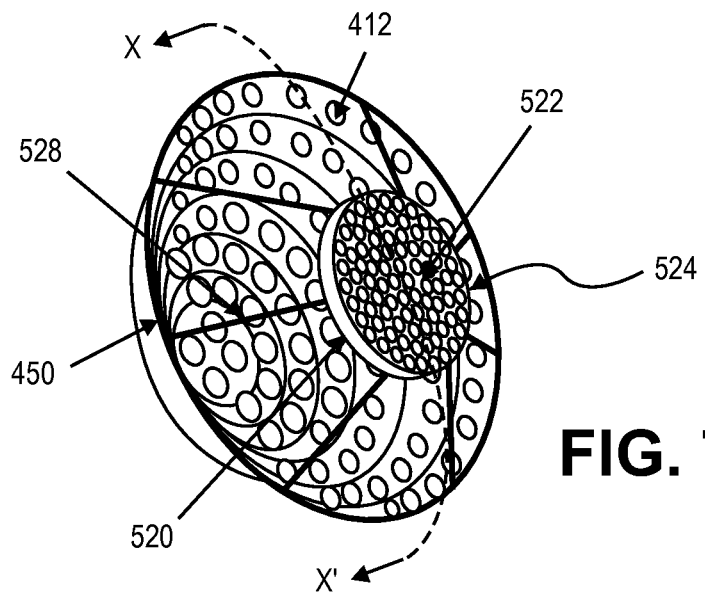

FIG. 7A is a schematic illustrations of an exemplary photoacoustic imaging device in accordance with various aspects of the disclosure.

Figure 7B:
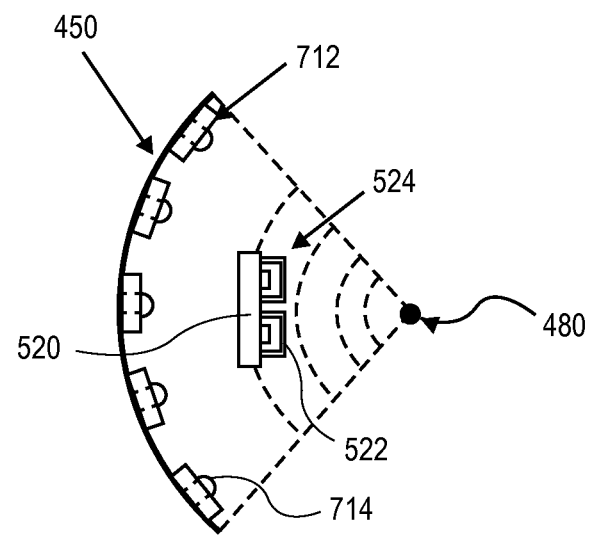

FIG. 7B is a cross-sectional view along line X-X' of FIG. 7A, wherein the light sources comprise diodes.

Figure 7C:
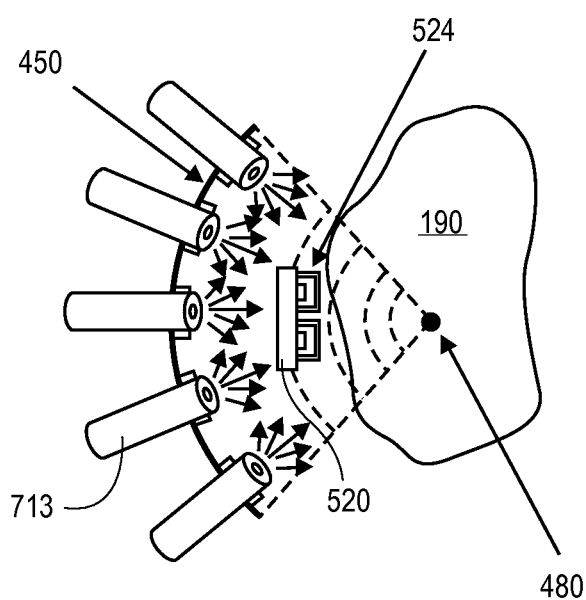

FIG. 7C is a cross-sectional view along line X-X' of FIG. 7A, wherein the light sources comprise optical fibers.

FIG. 8 is a schematic illustration of an exemplary photoacoustic imaging device in accordance with various aspects of the disclosure.

FIG. 9A is a schematic illustration of an exemplary photoacoustic imaging device in accordance with various aspects of the disclosure.

FIG. 9B is a cross-sectional view along line X-X' of FIG. 9A, wherein the light sources comprise optical fibers.

FIGS. 10A-10D are schematic illustrations of exemplary photoacoustic imaging modules in accordance with various aspects of the disclosure.

DETAILED DESCRIPTION

An exemplary embodiment of a photoacoustic imaging device with integrated arrays of infrared light sources and ultrasonic transducers is shown in FIGS. 1A-1C. According to various aspects of the disclosure, a photoacoustic imaging device 100 may comprise a first substrate 110 and a second substrate 120, with the second substrate 120 being stacked on the first substrate 110 and coupled to one another, for example, via wafer-to-wafer bonding. The stacked substrates 110, 120 may be electrically coupled with a printed circuit board 130 via bonding wire 132.

Ultrasonic transducers 122 may be integrated on the second substrate 120 in a one- or two-dimensional array 124. The second substrate 120 may comprise an infrared-transparent substrate such as, for example, silicon, glass, or polymer, such that infrared light illuminated from underneath the ultrasonic transducer substrate 120 can penetrate through the ultrasonic transducer substrate 120 and cast on target tissue without significant loss.

The first substrate 110 may comprise a substrate such as, for example, gallium arsenide (GaAs) or other compound semiconductor substrates. The first substrate 110 may include an array 116 of infrared light sources 112 such as, for example, an array of laser diodes 212 as shown in FIG. 1C. For example, the substrate 110 may comprise active layers of surface emitting laser diodes. According to other aspects, an array of optical fibers 312, as shown in FIG. 3, may be used for illumination of tissue 190. In some aspects, the light sources 112 may comprise an array of light emitting diodes (not shown).

As shown in FIGS. 1-3, an array of micro-lenses 114 may be used to spread the infrared light emitted from the light sources 112, for example, the laser diodes 212 or the optical fibers 312. Through the micro-lenses 114, the infrared beams will spread over a broader angle and will uniformly cast on a target area. Thus, the infrared light transmitted from the light source 212, 312 will travel through the ultrasonic transducer chip 120 to illuminate and stimulate target tissue 190, while the ultrasound generated from the infrared-stimulated tissue will be received by the ultrasonic transducers 122 on the front of the imaging device 100.

Referring to FIGS. 2A and 2B, fabrication of the micro-lenses 114 on top of the laser diodes 212 is shown. The micro-lenses can be constructed with a polymer such as, for example, polydimethylsiloxane (PDMS), using a photolithography and a post baking process. The micro-lenses 114 spread the infrared light emitted by the laser diodes 212. After distribution through the array of micro-lenses 114, the infrared light emitted by the laser diodes 212 may be more uniformly distributed across the intended viewing area, which may result in better images.

Referring again to FIGS. 3A-3C, a photoacoustic imaging module 300 may include a platform 310 that accommodates an array 316 of optical fibers 312. The platform 310 and the ultrasonic transducer substrate 120 can be coupled via wafer-to-wafer bonding. The light coming out from the optical fibers 312 can be more uniformly distributed over the intended imaging area by micro-lenses 114 on top of the optical fiber end port for light spread. The stacked platform 310 and substrate 120 may be electrically coupled with a printed circuit board 130 via bonding wire 132.

In a photoacoustic imaging process, the intensity of infrared light decreases as the light travels deeper inside tissue. The loss of infrared flux is mainly due to absorption and scattering by the tissue. After the intensity of infrared decreases to a certain level where it is no longer capable of starting a rapid thermal expansion, no information is available for photoacoustic imaging of the tissue at that depth. Similarly, where the infrared light is still capable of triggering a rapid thermal expansion but the amplitude of the ultrasound generated is too weak to be distinguished from the noise, no information is available for photoacoustic imaging of the tissue at that depth. These factors determine the maximum viewing depth of photoacoustic imaging. This maximum viewing depth is mainly determined by the infrared intensity and the ultrasound signal strength. While it seems plausible to increase the infrared illumination intensity in order to push this minimum detectable infrared intensity deeper insider the tissue, an upper limit of the maximum infrared intensity allowed to apply on a patient is set by the U.S. Food and Drug Administration (FDA) and American National Standards Institute (ANSI). Under the current ANSI standard, the maximum viewing depth of body organs or tissue via photoacoustic imaging is no more than 5-8 cm using a conventional photoacoustic imaging setup.

Referring now to FIGS. 4A and 4B, photoacoustic imaging devices in accordance with the disclosure may be designed to enhance the intensity of infrared radiation in tissue so as to increase the maximum viewing depth of a photoacoustic imaging process, while maintaining compliance with FDA and ANSI standards. As shown in FIG. 4B, a spherical shell 450 may include a converging array 416 of light sources 412. The shell 450 may comprise plastic, polymer, metal, or ceramics. The shell 450 with the converging array 416 of light sources 412 may be employed in a photoacoustic imaging device to enhance the light intensity for illumination of tissue 190 to compensate for the infrared intensity lost due to absorption and scattering by the tissue. The light sources 412 may be associated with and configured to emit infrared light from the inner surface 452 of the curved shell 450 and to converge at a focusing point 480.

The light sources 412 may comprise laser diodes, light emitting diodes, or optical fibers. In any event, as shown in FIG. 5, micro-lenses 514 may be associated with the light sources 412. Thus, the intensity of infrared light from the light sources 412 propagating into the tissue 190 is enhanced by the focusing process enabled by the curved shell 450, while the micro-lenses 514 spread the infrared light over a broader angle to more uniformly cast on a target area. The exemplary embodiments of FIGS. 4-9 partially compensate for the loss due to absorption and scattering by the body tissue/organ such that infrared intensity decreases less drastically as that of a uniform infrared beam with a planar wave-front.

Assuming that infrared light transmitted from the inner surface of the spherical shell is of uniform intensity $\phi_0$ (watt/cm$^2$) and the radius of the spherical shell is $r_o$, at point $X_1$ on the tissue surface which is of distance $d_1$ from the geometrical center of the shell, the infrared intensity is determined as (approximately, assuming there is no loss before reaching the tissue surface):

$$\phi_o[2\pi r_0^2(1-\sin\theta)] = \phi_1[2\pi(r_0-d)^2(1-\sin\theta)] \rightarrow \phi_1 = \qquad (1)$$
$$\phi_o \times \frac{2\pi r_0^2[1-\sin\theta]}{2\pi(r_0-d)^2[1-\sin\theta]} = \phi_o \frac{r_0^2}{(r_0-d)^2}$$

Now assuming $\Delta d = r_1 - r_2$ is infinitesimal, the infrared flux density at point $X_1$ is $\phi_1$, and the infrared flux density at point $X_2$ is $\phi_2$, (a) If considering only the infrared absorption and scattering by the tissue, and neglecting the infrared converging effect caused by the curved infrared shell, the difference of light intensity at $X=X_2$ and $X=X_1$ is $$\Delta\phi = \phi_2 - \phi_1 = \frac{d\phi}{dx}\Delta x = -\alpha\phi(x)\Delta x \qquad (2)$$

where $\alpha$ is coefficient including both infrared absorption in tissue and scattering.

(b) If considering only the infrared converging effect caused by the curved shell and neglecting the tissue absorption and scattering, $$\phi_2 = \phi_1 \times \frac{r_1^2}{r_2^2} \qquad (3)$$

$$\Delta\phi = \phi_2 - \phi_1 = \phi_1\left(\frac{r_1^2}{r_2^2}-1\right) = \phi_1\left[\frac{r_1^2}{(r_1-\Delta d)^2}-1\right] =$$
$$\phi_1\left[\frac{1}{\left(1-\frac{\Delta d}{r_1}\right)^2}-1\right] = \phi_1\left[\frac{1}{\left(1-2\frac{\Delta d}{r_1}+\frac{(\Delta d)^2}{r_1^2}\right)}-1\right]$$

$$\rightarrow \phi = \phi_1 \left[ \frac{2\frac{\Delta d}{r_1} - \frac{(\Delta d)^2}{r_1^2}}{\left(1 - 2\frac{\Delta d}{r_1} + \frac{(\Delta d)^2}{r_1^2}\right)} \right] \quad (4)$$

For the special case when $r_1 \gg \Delta d$ $$\Delta\phi = \phi_2 - \phi_1 = \phi_1 \left( \frac{r_1^2}{r_2^2} - 1 \right) = \phi_1 \left[ \frac{r_1^2}{(r_1 - \Delta d)^2} - 1 \right] = \quad (5)$$

$$\phi_1 \left[ \frac{1}{\left(1 - \frac{\Delta d}{r_1}\right)^2} - 1 \right] \approx \phi_1 \left[ 1 + 2\frac{\Delta d}{r_1} - 1 \right] = \frac{2(\Delta d)\phi_1}{r_1}$$

From this equation it is seen that $\Delta\phi$ is positive (gaining intensity in the course of propagation deeper inside the tissue) and proportional to $$\frac{1}{r} \text{ (under the condition } r \gg \Delta d\text{)}.$$

(c) Now, considering shell converging and tissue absorption and scattering simultaneously, $$\frac{d\phi(x)}{dx} = -\alpha\phi + \frac{2\phi}{r_1} = \phi \cdot \left[ -\alpha + \frac{\frac{2}{r_1} - \frac{(\Delta d)}{r_1^2}}{\left(1 - 2\frac{\Delta d}{r_1} + \frac{(\Delta d)^2}{r_1^2}\right)} \right] \quad (6)$$

This equation can be solved by finite element analysis.
(4) For the special case when $r_1 \gg \Delta d$, $$\frac{d\phi(x)}{dx} = -\alpha\phi + \frac{2\phi}{r_1} = \phi \cdot \left[ -\alpha + \frac{2}{r_1} \right] \quad (7)$$

From this equation, it can be seen that the flux loss due to absorption and scattering can be partially compensated by the light converging mechanism enabled by a curved light source. As a result, the boundary point where infrared illumination is too weak to trigger a detectable photoacoustic imaging process can be pushed deeper inside the tissue. According to a finite element simulation conducted by applicant, with such a curved light source, the viewing depth of photoacoustic imaging can be extended to more than 10 cm.

The curvature of the shell, for example, the radius of the shell for a spherical shell, along with the maximum infrared intensity allowed to apply on the surface of the tissue and the absorption coefficient α determine the maximum viewable depth in a photoacoustic imaging process. For a spherical shell, a larger sphere radius will produce a larger viewing angle, but will result in a poorer converging effect and reduce the maximum viewing depth. A smaller sphere radius produces a smaller viewing angle, but will result in a better converging effect and increase the maximum viewing depth.

Referring again to FIG. 5, a photoacoustic imaging device 500 includes the spherical shell 450 and the associated light sources 412 for illumination of tissue 190. The imaging device 500 also includes an array 524 of ultrasonic transducers 522 integrated on an infrared-transparent substrate 520 such as, for example, silicon, glass, or polymer. The transducers 522 receive the ultrasound in a photoacoustic imaging process. The substrate 520 with an array 524 of ultrasonic transducers 522 is placed in front of the light sources 412 in order to more efficiently receive ultrasound transmitted from the tissue 190. The substrate 520 with the ultrasonic transducer array 524 may be coupled with the shell 450 and light sources 412 by connecting members 528 (FIG. 6) such as, for example, infrared-transparent rods. The connecting members 528 may comprise polymer or plastic. At least a portion of the infrared light will propagate through the supporting rods 528, the substrate 520, and the ultrasonic transducer array 524 before reaching the tissue.

Referring now to FIGS. 6 and 7, an exemplary photoacoustic imaging process with extended viewing depth is depicted. As shown, target tissue 190 is illuminated with infrared light from the array 416 of light sources 412. The array of infrared light sources 412 may be associated with the inner surface 452 of the curved shell for illuminating the tissue 190. The target tissue 190 then generates ultrasound, which can be detected by the array 524 of ultrasonic transducers 522. The detections made by the array 524 of ultrasonic transducers 522 can then be directed to a processor and/or microcontroller (not shown), which can then generate an image representative of the target tissue 190 and/or provide diagnostic information based on the received ultrasonic transmissions.

The light sources 412 can be laser diodes 712, as shown in FIG. 7B, light emitting diodes (not shown), or optical fibers 713, as shown in FIG. 7C. In the various aspects, a miniature lens 714, for example, a microfabricated polymer lens, may be placed in a path of illumination from each light source 412 to spread the light so that the light can be more evenly cast on the target tissue 190.

According to various aspects, as shown in FIGS. 8 and 9, light sources can also be installed on a planar platform configured to converge light for photoacoustic imaging. Referring to FIG. 8, a photoacoustic imaging device 800 may include a substantially planar frame 860. The frame 860 may comprise plastic, polymer, metal, or ceramics. The frame 860 may be coupled to a substrate 820 comprising an array of ultrasonic transducers (not numbered) via one or more connecting members 828, for example, infrared-transparent rods. The connecting members 828 may comprise polymer or plastic. Infrared light sources 812, for example, laser diodes, light emitting diodes, or optical fibers, can be arranged on the frame 860 in an orientation that results in converging illumination. For example, each light source 812 may be tilted at a different angle with respect to the plane of the frame 860 such that the infrared beams converge toward a target area similar to the curved spherical shells. Micro-lenses 814 may be associated with the light sources 812 to spread the light so that the light can be more evenly cast on a target. FIG. 9A illustrates an exemplary aspect where the light sources 812 comprise laser diodes 912 extending through the frame 860, and FIG. 9B illustrates an exemplary aspect where the light sources 812 comprise optical fibers 913 extending through the frame 860.

Figure 10A:
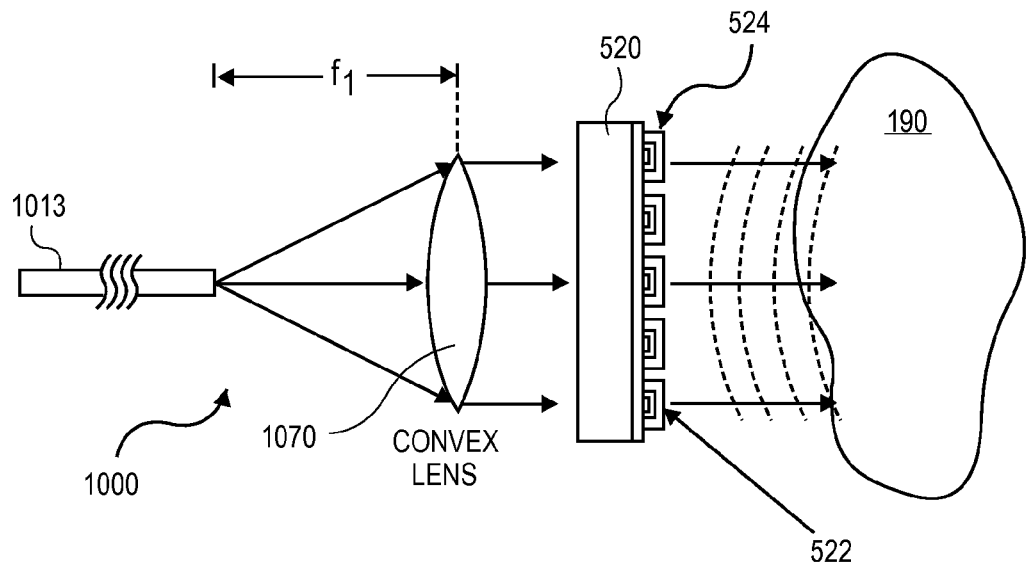
Figure 10B:
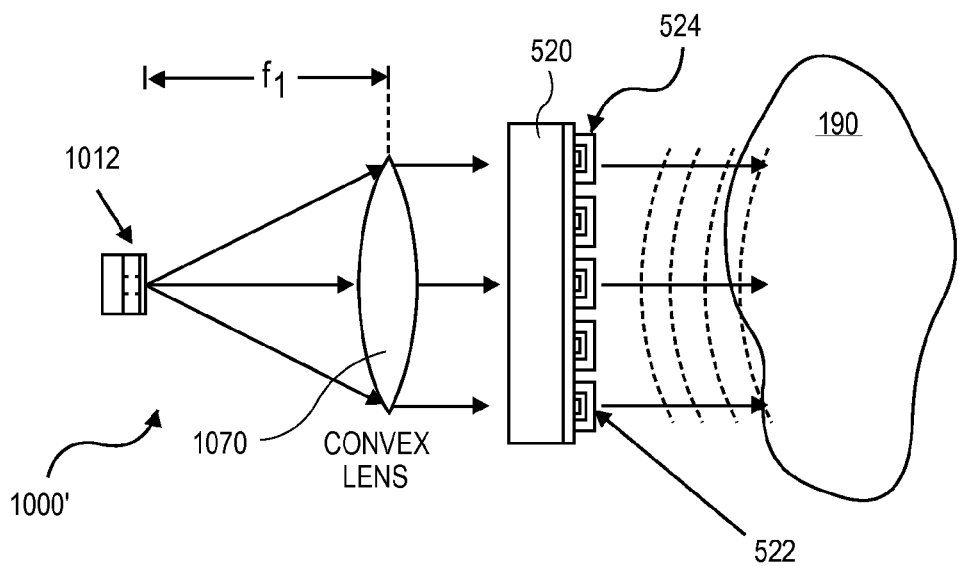

FIGS. 10A-10D show exemplary photoacoustic imaging modules 1000, 1000', 1000'', 1000''' in accordance with various aspects of the disclosure. The exemplary modules may comprise "system-in-a-package" photoacoustic imaging modules. FIGS. 10A and 10B illustrate photoacoustic imaging modules 1000, 1000' having one convex lens 1070 arranged to reconfigure light emerging from one light source or an array of light sources. According to various aspects, the light source may comprise, for example, an optical fiber 1013 (FIG. 10A) or a diode 1012 (FIG. 10B), such as a laser diode or a light emitting diode. The convex lens 1070 is arranged to reconfigure light from the light source(s) 1012, 1013 into a large-area Gaussian beam for illuminating a target tissue 190. The light source or array of light sources 1012, 1013 is placed at the focal point of the convex lens. The profile of the light beam coming out from an optical fiber (or a laser diode or a light emitting diode) is Gaussian, but with a small area. Through the convex lens 1070, the small-area Gaussian beam is reconfigured into a large-area Gaussian beam according to the following equation:

$$\text{Beam Size}=2*f_1*\sin(2\theta) \qquad (8)$$

where $f_1$ is the focal length of the convex lens 1070, and $\theta$ is the angular extent of the beam at a specified percentage of peak irradiance of the beam profile of the light source 1012, 1013 (e.g., the optical fiber/laser-diode/light-emitting-diode beam profile). The light profile of the beam, after passing through the convex lens, is also Gaussian, but with a larger spot size. Through appropriate choice of the lens focal length and aperture size, a profile suitable for photoacoustic imaging can be obtained. Light coming out from the light sources 1012, 1013 is thus reconfigured through the convex lens 1070 and cast on the target tissue 190 through the capacitive micromachined ultrasonic transducer array 524 chip. The convex lens 1070 converts light from a point source (e.g., outlet of an optical fiber or diode) into uniformly-distributed parallel light for tissue illumination.

Figure 10C:
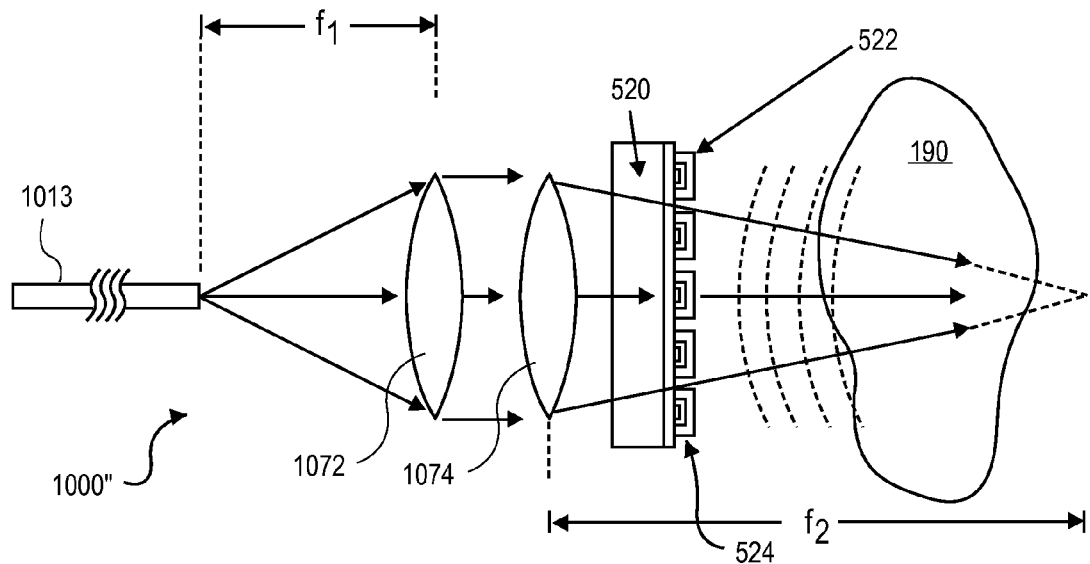
Figure 10D:
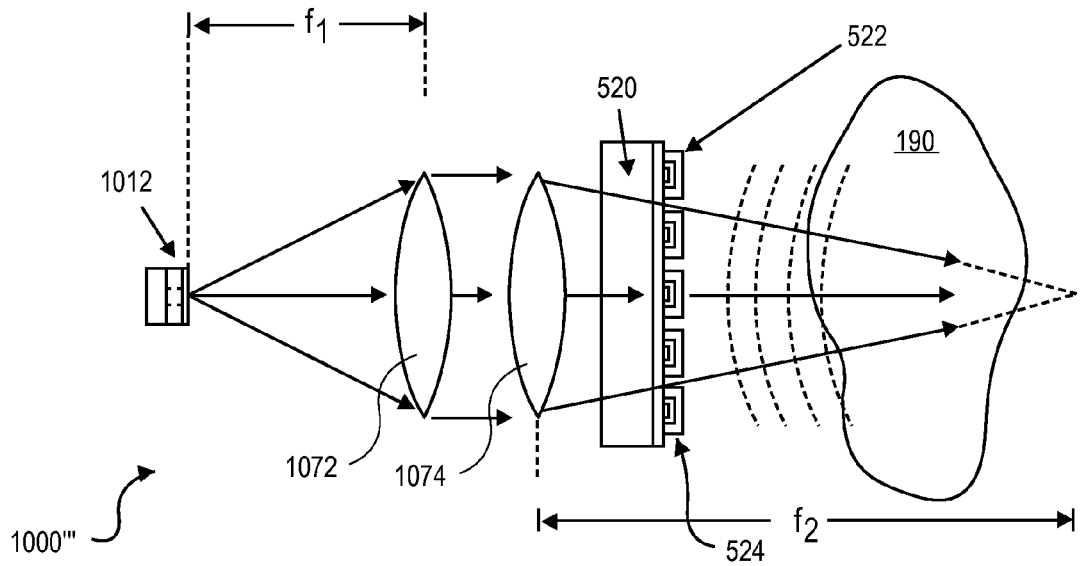

With two cascade convex lenses 1072, 1074, photoacoustic imaging devices 1000'', 1000''' can provide a converging light beam configured for photoacoustic imaging as shown in FIGS. 10C and 10D, respectively. It may be beneficial to use a converging light beam in a photoacoustic imaging process so that the light energy may be enhanced during the course of propagation for penetration deeper into the tissue. Light coming out from an optical fiber is converted into a converging beam using two or multiple convex lenses 1072, 1074. Through this focusing mechanism, the energy loss of light in tissue due to absorption and scattering can be partially compensated with the converging process, and the effective viewing depth of PAI can be increased. That means, at a deeper (compared to the case using a parallel light beam without focusing mechanism) depth in tissue the light intensity is still strong enough to trigger a thermal elastic expansion of tissue that generates detectable ultrasound. FIG. 10C illustrates an optical fiber light source 1013, while FIG. 10D illustrates a diode light source 1012. A system-in-a package photoacoustic imaging module distributing a converging light beam for tissue illumination. It should be appreciated that photoacoustic imaging modules in accordance with this disclosure may include more than two convex lenses for converging the light beam.

According to various aspects, a CMUT probe for photoacoustic imaging may comprise a large, 1-D or 2-D CMUT array, which will greatly increase the data acquisition speed for a given aperture size. Furthermore, the CMUT array geometries such as, for example, a ring array have the practical benefit that the laser light can come through the hole in the center of the array. Typically, the CMUT structure is composed of a dielectric layer between two electrodes in order to avoid the electric short in the operation. The big problem with such a CMUT structure is that the bulk or surface of such dielectrics can be charged up locally. This accumulated parasitic charge may alter actuation voltages and change the mechanical behaviors. A most straightforward method to decrease the effect of dielectric charging is to use a bipolar AC rather than DC voltage actuation. However, the charging effect cannot be eliminated completely and more complex actuation electronics are required.

According to various aspects, a different CMUT structure may comprise a polysilicon membrane suspended above a vacuum-sealed gap. No dielectric layer is inserted between the membrane and its counter polysilicon electrode. In order to prevent shorting of the membrane to its counter electrode, an array of dielectric posts is added on top of the polysilicon counter electrode. The dielectric posts have been reported to alleviate the charge trapping very effectively [see J. Chen, X. Cheng, C. Chen P. Li, J. Liu, and Y. Cheng, "A Capacitive Micromachined Ultrasonic Transducer Array for Minimally Invasive Medical Diagnosis" *IEEE Journal of Microelectromechanical Systems*, vol. 17, no. 3, pp. 599-610, June 2008]. Compared to a nitride-membrane CMUT device with a thin-film metal electrode covered on top of the silicon nitride membrane, the use of a conductive polysilicon membrane also reduces the effective gap distance and therefore the driving voltage. In addition, polysilicon has been widely used for fabricating many different kinds of transducers. The control of the mechanical properties of polysilicon has been studied extensively and is relatively well understood.

An exemplary process for fabricating a CMUT device may comprise a two-layer polysilicon surface micromachining process modified from a conventional Multi-User Micro-Electro-Mechanical Process (MUMP). Some differences between the exemplary process described herein and the MUMP are: (1) the gap distance between POLY1 and POLY0 was reduced to 0.18 pm such that the CMUT device can have a better sensitivity at a low DC bias for ultrasound reception; (2) the thickness of POLY1 layer was reduced to 1.0 and 1.2 μm such that the membrane vibrates at the desired acoustic frequency and delivers acoustic pressure suitable for medical diagnoses; (3) a thin silicon nitride layer was added on top of POLY0 counter electrode for insulation purpose; and (4) a 1.1 μm-thick parylene C layer was added on top of the POLY1 membrane as the passivation layer.

The fabrication of a CMUT device starts with an n-type, <100> silicon wafer. The wafer is doped with phosphorus using a diffusion process at about 975° C. for about 30 minutes to form a highly conducting surface. This conducting layer is useful for reducing charge buildup for the electrostatic devices to be built on this platform. A layer of silicon dioxide, typically 2.0 μm thick, is grown using a wet oxidation process at about 1100° C. Onto the wafer is then deposited 0.2 μm of silicon nitride, and 0.5 μm of polysilicon. The polysilicon film is doped with phosphorus using a diffusion process at about 975° C. for about 30 minutes. This layer will be used to define the counter electrodes and anchoring pads of the CMUT devices. Next, another layer of silicon nitride, for example, nominally 800 Å thick, is deposited using LPCVD. This nitride layer may be patterned using photolithography and reactive ion etching to form an array of nitride posts on top of the polysilicon counter electrode. For a study about the impact of nitride film on the charging problem of this CMUT device, the polysilicon counter electrodes of some devices are completely covered with the 800 Å-thick nitride film instead of a dielectric post array. The post is designed to prevent shorting of the membrane and the counter electrode during ultrasonic transduction.

The polysilicon layer is next patterned and dry etched to form the counter electrodes and the anchoring pads of the CMUT devices. A layer of sacrificial phosphosilicate glass (PSG), for example, nominally 2100 Å thick, is deposited next using LPCVD. The thickness of this sacrificial oxide layer is reduced to approximately 1800 Å after a post-densification annealing process at about 1000° C. for about 60 minutes in nitrogen gas. The densification process reflows the PSG film and appreciably reduces the density of surface bubbles on the PSG film. The PSG film is then patterned and dry etched to open the anchor holes, over which the polysilicon microstructures will attach to the substrate. A polysilicon film having a thickness of about 1.0 or 1.2 µm is next deposited using LPCVD. This polysilicon film is doped with phosphorous using a diffusion process at about 975° C. for about 45 minutes and annealed at about 1050° C. for about 60 minutes to activate the dopants and relieve residue stress. This structural polysilicon film is patterned using photolithography and reactive ion etching to form the membrane structure.

The sacrificial PSG is completely removed in release etching process using 49% HF solution. The etch rate of PSG in 49% HF is about 36000 Å/min at 25° C. for the PSG film exposed to HF in an open solution. The etching rate of PSG in HF is slower in a narrow cavity when the diffusion of the etching chemical in and out of the cavity limits the etching process. For CMUT releasing, the release etching time varies with the gap dimension, including the diameter of the membrane and the gap height. It takes approximate 2 minutes to fully release a membrane with 46 µm in diameter and 0.2 µm in gap distance. A surpercritical drying process is next used to dry the device after the wet release process. The release holes are then sealed in vacuum using PECVD oxide. Sealing the gaps enables immersive operation of CMUT. With a sealed gap, water or fluids outside of the CMUT device is blocked from entering the gap, preventing the hydrolysis of water in the cavity under high electric fields. The thickness of PECVD oxide used to seal the release hole was 3.0 µm. A photolithography process and wet etch are then used to pattern this sealing oxide. The sealing oxide is completely removed on all areas except the areas around the release holes. The next step of the membrane sealing is negative tone photo-resist coating and patterning for metal liftoff and Cr/Au sputtering (400 Å/4000 Å). Chromium (Cr) may be used to improve adhesion. While thermal evaporation is used more commonly in the lab, sputtering can provide a better step coverage. The sputtered metal layer goes through the standard liftoff process before passivation. A 1 µm Parylene C as passivation layer is coated using PVD2010 afterwards.

For biomedical invasive applications, especially for the implantable devices, the dimension must be miniaturized in order to reduce the disruption of the tissue during operation. The substrate is micro machined using a masked double-sided dry etching process as described in X. Cheng, J. Chen etc. "Fabrication and Assembly of A Monolithic 3D CMUT Array for Imaging Applications" *IEEE Ultrasonic Symposium*, New York, October 2007; J. Chen, X. Cheng, C. Chen P. Li, J. Liu, and Y. Cheng, "A Capacitive Micromachined Ultrasonic Transducer Array for Minimally Invasive Medical Diagnosis" *IEEE Journal of Microelectromechanical Systems*, vol. 17, no. 3, pp. 599-610, June 2008, both of which are incorporated herein by reference in their entirety. FIGS. 13(*a*) and 13(*b*) are SEM photographs of a released 1-D polysilicon CMUT array having a rectangular shape and a circular shape, respectively.

Therefore, in accordance with various aspects of this disclosure, a photoacoustic imaging module may integrate a broad-area infrared light source with a MEMS-based ultrasonic transducer array in a package for medical imaging. Similar to a camera with a built-in flashlight, the relative position between the infrared light source and the ultrasonic transducers on the module may be accurately aligned and both devices are aimed at the target direction. This PAI module can therefore be directly placed on the skin of a patient for imaging and no light-source to ultrasound transducer alignment is needed. With an integrated front-end signal-processing circuit, this portable module may be able to provide real-time 3-D photoacoustic image of tissue/organ for clinical use. The 3-D image acquired may be displayed in real-time and can be stored in a personal computer, or any other memory storage device, for future review. In additional to photoacoustic imaging, this module can also provide pulse-echo ultrasound imaging in parallel with photoacoustic imaging, thus offering complementary diagnostic information.

In use, light transmitting from a light source such as an optical fiber or a diode is reconfigured through one or multiple convex lenses and cast on the target tissue through the capacitive micromachined ultrasonic transducer array chip. In the case of a single convex lens, light is converted from a small-area source (outlet of an optical fiber) into a large-area Gaussian profile for tissue illumination. The chip in this package may contain one- or two-dimensional ultrasonic transducer array for ultrasound reception. The ultrasonic transducers are integrated on an infrared-transparent substrate, e.g., a silicon or glass substrate, such that infrared illuminating from underneath the ultrasonic transducer chip can penetrate through the ultrasonic transducers as well as their substrate and cast on the target tissue without significant loss. While the metal interconnects on the ultrasonic transducer array would obstruct part of the infrared, the small area percentage of these metal interconnects over the total transducer area makes this blockage insignificant to the photoacoustic imaging process In the case of multiple convex lenses, the light is first converted from a small-area source into a large area profile, but is then converged to compensate for the energy loss of light in tissue due to absorption and scattering upon deeper penetration into the target tissue.

It will be apparent to those skilled in the art that various modifications and variations can be made to the photoacoustic imaging devices and methods of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A photoacoustic imaging module comprising:
a light source configured to emit a light beam in a direction of a target tissue;
an ultrasonic transducer array of ultrasonic transducers integrated in a side of a substrate, the ultrasonic transducer array configured to receive ultrasound generated by rapid thermal expansion of the target tissue, each ultrasonic transducer being a capacitive micromachined ultrasonic transducer; and
a lens between the light source and the ultrasonic transducer array, the lens being a convex lens or a spreading lens, the lens arranged with respect to the light source and the ultrasonic transducer array such that the light beam directed from the lens passes through ultrasonic transducers of the ultrasonic transducer array in addition to passing through the substrate from a surface of the substrate opposite the side of the substrate on which the ultrasonic transducers are integrated through the ultrasonic transducers including a membrane of each of the respective ultrasonic transducers to the target tissue to excite the target tissue, the lens being arranged to expand the area profile of the light beam to illuminate the target tissue and cause rapid thermal expansion.

2. The photoacoustic imaging module of claim 1, wherein the ultrasonic transducer array is integrated on an infrared-transparent substrate.

3. The photoacoustic imaging module of claim 1, wherein the light source comprises one of an optical fiber, a laser diode, or a light emitting diode.

4. The photoacoustic imaging module of claim 1, wherein the light source comprises an array of one of optical fibers, laser diodes, or light emitting diodes.

5. A photoacoustic imaging module comprising:
a light source configured to emit a light beam in a direction of a target tissue;
an ultrasonic transducer array of ultrasonic transducers integrated in a side of a substrate, the ultrasonic transducer array configured to receive ultrasound generated by rapid thermal expansion of the target tissue, each ultrasonic transducer being a capacitive micromachined ultrasonic transducer; and
a plurality of convex lenses between the light source and the ultrasonic transducer array, the convex lenses arranged with respect to the light source and the ultrasonic transducer array such that the light beam directed from the convex lenses passes through ultrasonic transducers of the ultrasonic transducer array in addition to passing through the substrate from a surface of the substrate opposite the side of the substrate on which the ultrasonic transducers are integrated through the ultrasonic transducers including a membrane of each of the respective ultrasonic transducers to the target tissue to excite the target tissue, the convex lenses being arranged to first expand the area profile of the light beam and then to converge the light beam so as to illuminate the target tissue, increase depth of penetration by the light beam, and cause rapid thermal expansion of the target tissue.

6. The photoacoustic imaging module of claim 5, wherein the ultrasonic transducer array is integrated on an infrared-transparent substrate.

7. The photoacoustic imaging module of claim 5, wherein the light source comprises one of an optical fiber, a laser diode, or a light emitting diode.

8. The photoacoustic imaging module of claim 5, wherein the light source comprises an array of one of optical fibers, laser diodes, or light emitting diodes.

9. A photoacoustic imaging device comprising:
an array of light sources configured and arranged to illuminate a target tissue; and
an array of ultrasonic transducers between the array of light sources and the target tissue, the ultrasonic transducers integrated in a side of a substrate, each ultrasonic transducer being a capacitive micromachined ultrasonic transducer, the array of transducers being fixedly coupled to the array of light sources such that light from the array of light sources passes through ultrasonic transducers of the array of ultrasonic transducers in addition to passing through the substrate from a surface of the substrate opposite the side of the substrate on which the ultrasonic transducers are integrated through the ultrasonic transducers including a membrane of each of the respective ultrasonic transducers to the target tissue to excite the target tissue, when illuminating the target tissue, the array of ultrasonic transducers being configured and arranged to receive ultrasound transmissions from the target tissue in response to light from the array of light sources illuminating the target tissue.

10. The photoacoustic imaging device of claim 9, wherein the array of light sources is arranged on a surface of a spherical shell.

11. The photoacoustic imaging device of claim 10, wherein the array of light sources is arranged in a manner such that light transmitted from the light sources converges at the target tissue.

12. The photoacoustic imaging device of claim 9, wherein the array of light sources is arranged on a substantially planar support.

13. The photoacoustic imaging device of claim 12, wherein the array of light sources is arranged in a manner such that light transmitted from the light sources converges at the target tissue.

14. The photoacoustic imaging device of claim 9, wherein the array of light sources is configured to emit infrared illumination.

15. The photoacoustic imaging device of claim 9, wherein the array of light sources are configured and arranged to illuminate the target tissue with light in a selected wavelength range to trigger a rapid thermoelastic expansion of the target tissue to generate the ultrasound transmissions received by the array of ultrasound transducers.

16. The photoacoustic imaging module of claim 2, wherein the infrared-transparent substrate is a silicon substrate.

17. The photoacoustic imaging module of claim 2, wherein the infrared-transparent substrate is a glass substrate.

18. The photoacoustic imaging module of claim 1, wherein each capacitive micromachined ultrasonic transducer includes a silicon membrane.

* * * * *